United States Patent [19]

van Zelm

[11] 4,231,603
[45] Nov. 4, 1980

[54] GRIPPING DEVICE FOR HANDICAPPED PERSONS

[76] Inventor: Willem D. van Zelm, 1005 Boyce Ave., Baltimore, Md. 21204

[21] Appl. No.: 12,336

[22] Filed: Feb. 15, 1979

[51] Int. Cl.³ .......................... A47F 13/06; B25J 13/02
[52] U.S. Cl. .................................................. 294/19 R
[58] Field of Search ................... 294/19 R, 11, 20, 22, 294/50.5, 50.6, 50.8, 50.9, 65.5, 100, 104, 106, 110 A, 115; 403/93, 91, 97, 157

[56] References Cited

U.S. PATENT DOCUMENTS

| | | | |
|---|---|---|---|
| 3,146,015 | 8/1964 | Koberge | 294/65.5 |
| 3,199,905 | 8/1965 | Johnson | 294/19 R |

FOREIGN PATENT DOCUMENTS 628850 10/1961 Canada ...................................... 294/19

*Primary Examiner*—James B. Marbert
*Attorney, Agent, or Firm*—Walter G. Finch

[57] ABSTRACT

The invention is an improved gripping device for use by handicapped persons. The gripping device consists of double acting jaws that grips the item to be picked up or lifted, a forward arm section, a rearward arm section, and a control mechanism to control the gripping action of the double acting jaws and the hinge action between the forward arm section and the rearward arm section. The device can be operated with one hand. It can also be operated from a wheel chair.

9 Claims, 5 Drawing Figures

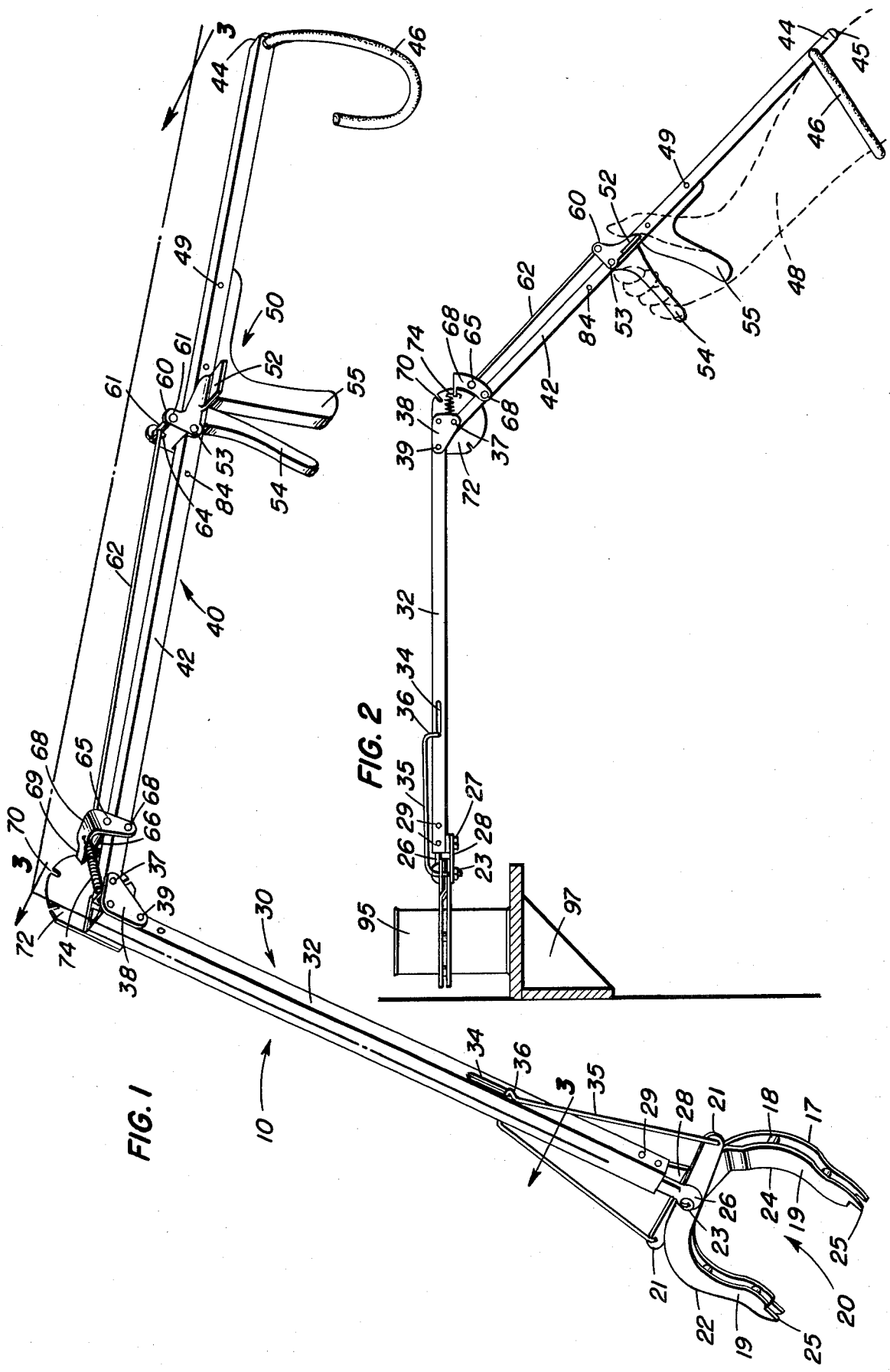

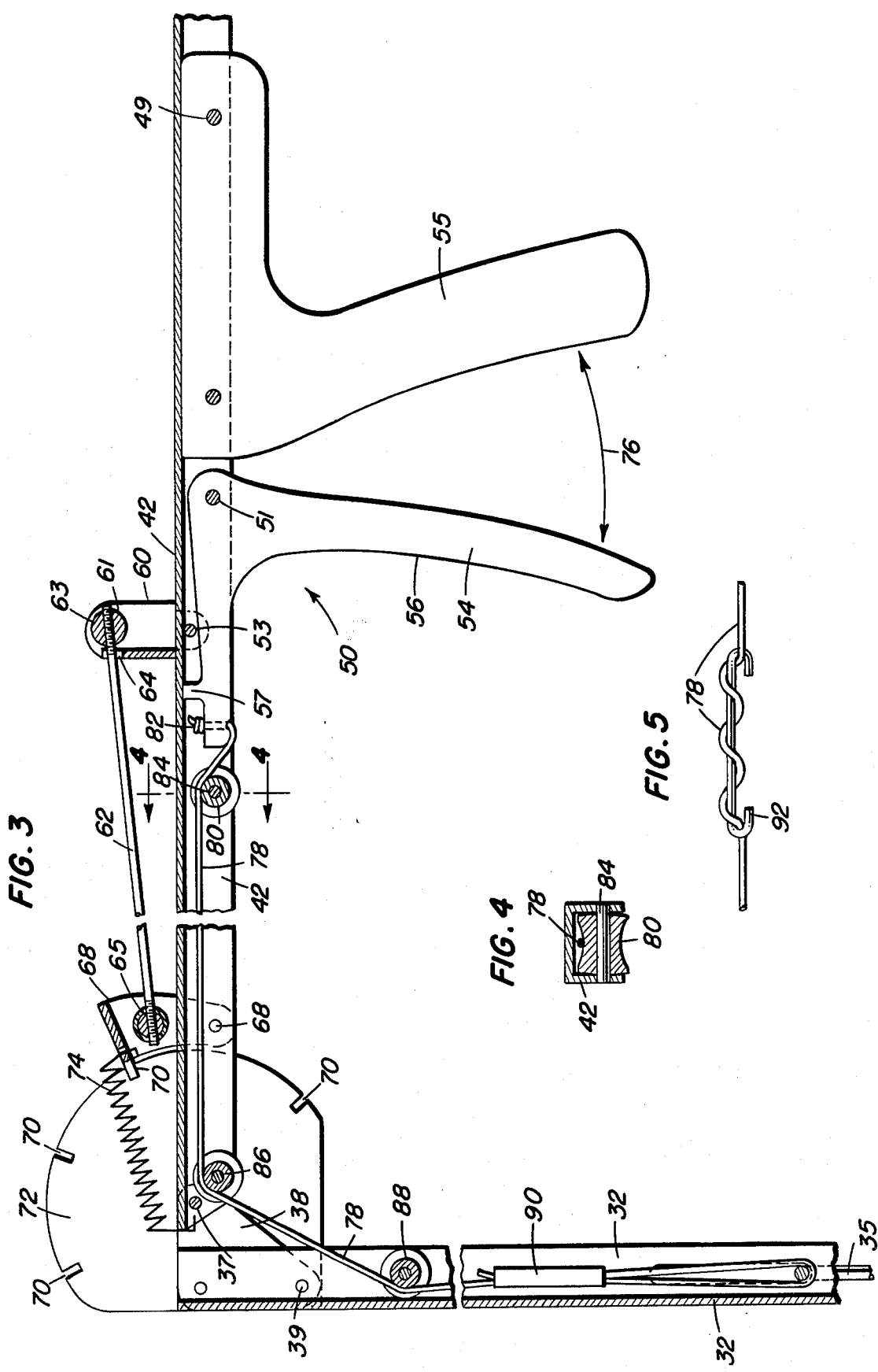

GRIPPING DEVICE FOR HANDICAPPED PERSONS

BACKGROUND AND SUMMARY OF THE INVENTION

The invention relates to devices used by handicapped persons, and in particular to devices that extend the range of the handicapped person's reach. Specifically, it is a gripping device for picking up or lifting items and moving them about the area.

A need has existed for a device that handicapped persons can use conveniently, is light in weight, easy to operate, can be operated with one hand, can be used from a wheelchair, and which brings an item directly to the user. The present invention meets these characteristics.

In the prior art, there have been pick-up type devices, however, the devices have been of rather short reach, provided only a short support at the hand, are of a single direction pick-up with no flexibility to move the object to the user conveniently, often require two hands for operation, and in general, do not have the flexibility of the present invention.

It is, therefore, an object of the invention to provide a gripping device for handicapped persons that is light in weight.

It is another object of the invention to provide a gripping device for handicapped persons that may be operated with one hand.

It is also an object of the invention to provide a gripping device for handicapped persons that has a capability of bringing the lifted object back to the user.

It is still another object of the invention to provide a gripping device for handicapped persons that has a long arm support capability.

It is yet another object of the invention to provide a gripping device for handicapped persons that can be operated from a seated position, such as in a wheel chair.

Further objects and advantages of the invention will become more apparent in the light of the following description of the preferred embodiments.

BRIEF DESCRIPTION OF THE DRAWINGS

FIG. 1 is a perspective view of a gripping device for handicapped persons;

FIG. 2 is a side view of a gripping device for handicapped persons showing one method of picking up an object;

FIG. 3 is an enlarged partial section view on line 3—3—3 of FIG. 1;

FIG. 4 is a cross section view of a cable and roller support on line 4—4 of FIG. 3.

FIG. 5 is a side view of the "C" type takeup wire.

DESCRIPTION OF THE PREFERRED EMBODIMENT

Referring to the drawings and particularly to FIG. 1, a new and improved gripping device for handicapped persons is shown at 10.

The gripping device 10 has four major sections: a double acting jaws section 20, a forward arm section 30, a rearward arm section 40, and a control mechanism 50.

Turning first to the double acting jaws section 20, there are two jaws 22 and 24 that are hinged together by connector 23. The connector 23 permits the jaws 22 and 24 to swing together and to open in a scissor-like fashion at the connector 23.

The connector 23 may be a bolt and nut, a double headed rivet-like pin, a pin with a retaining means, or any similar connecting means that can be brought to holding position without compacting the jaws 22 and 24 so tightly together that freedom of scissor-like movement is prevented.

It is to be noted that the range of the aforementioned means for the structure of said connector 23 is within the scope and intent of this invention.

Continuing with the structure at the connector 23, a yoke-like holding bracket is formed to hold the jaws 22 and 24 with the connector 23 in an aligned position with forward arm section 30. Said yoke-like holding bracket consists of a top or outer bracket piece 26 and a lower or inner bracket piece 28. The yoke-like bracket is formed by connecting the lower or inner bracket piece 28 to the top or outer bracket piece 26 by suitable means 27, then fastening the fabricated yoke-like bracket with suitable means 29 within the end portion of the forward arm 32 of the forward arm section 30.

To provide ease of scissor-like action while maintaining sufficient rigidity between jaws 22 and 24, Teflon washers are placed between top bracket piece 26 and 22, between jaws 22 and 24, and between jaw 24 and lower bracket 28.

A single wire spring 35, passing through slot 34 in the forward arm 32, has a right angle bend 36 to maintain the relative position of the spring 35 centered in the slot 34 in relation to the forward arm 32. The two free ends of spring 35 connect to the inboard ends 21 of jaws 22 and 24 by providing hooked ends on said spring 35 and passing hooked ends through suitable clearance holes in the inboard ends 21 of jaws 22 and 24. Said hooked ends of spring 35 may be further bent to retain them in place, upsetting the ends of spring 35 to retain them in place, providing a nut on said ends, or by any other suitable means. Any such variation to retain said ends of spring 35 in place in the clearance holes in the inboard ends 21 is within the scope and intent of this invention.

It is to be noted that jaws 22 and 24 are shown in FIG. 1 as being fabricated of two flat pieces 17 and 19 with spaces 18 separating them. However, it is to be understood that, instead of said flat pieces 17 and 19 spaced apart by spaces 18, the jaws 22 and 24 may be a single solid bar configured the same as flat pieces 17 and 19, or a channel or "T" or other similar shape and configured to the shape of said flat pieces 17 and 19. The interior gripping area or surface of jaws 22 and 24 is lines or covered with a plastics, rubber-like material or other composition material (not shown on drawing) to enhance the pick-up characteristics of the double acting jaws section 20. The lining may be dimpled, serrated, or otherwise surface treated, molded, or worked to provide a better gripping surface.

The forward arm 32 is connected to the rearward arm 42 by a pair of gusset plates 38, one gusset plate 38 on each side of forward arm 32. Gusset plates 38 are rigidly attached to forward arm 32 by suitable means at two points of said gusset. The third point of said gusset is used for a pin 37 that serves as a pivot point about which the forward arm 32 and the rearward arm 42 rotate within a fixed or restricted arc in relation to each other and by which said forward arm 32 and rearward arm 42 are pivotally connected to each other.

The rearward arm 42 extends beyond the control mechanism 50 a sufficient distance so that the rearmost end 44 is near the users elbow. A plug cap 45 is inserted in the rearmost end 44 of the rearward arm 42.

An arm loop 46 is pivotally connected to the rearmost end 44 near the plug cap 45. The arm loop 46 is a more or less rigid wire-like structure configured in a more or less semicircular shape into which the arm near the elbow is rested while the hand grips the control mechanism 50. The arm loop 46 is covered with a plastics or rubber-like material for comfort of the user and for enhancing the holding snugness on the arm.

The arm loop 46 is shown installed in the rearmost end 44 of the rearward arm 42 for a right-handed user. The arm loop 46 may be installed from the opposite side of rearward arm 42 for a left-handed user. The arm loop 46 is retained in place in the rearward arm 42 by suitable means, such as pinching the end where it protrudes through the rearward arm 42, or upsetting the end, threading the end and adding a nut or other similar and suitable means.

The right hand 48 of a user is shown in dotted lines in FIG. 2, with fingers and thumb on the control mechanism 50, described hereinafter, and the arm 48 near the elbow resting in the arm loop 46 as hereinbefore mentioned. The arm loop 46 steadies the gripping device 10 when it is in use by having the effect of making the gripping device 10 and extension of the users arm 48. The arm loop 46 takes part of the strain off of the wrist of the user when picking-up or lifting a heavy object.

Turning now to the control mechanism 50, a general view is seen in FIGS. 1 and 2 with a detailed cross section shown in FIG. 3.

As shown in FIG. 2, the control mechanism 50 is arranged for a right handed person. The thumb lever 52 for control of the relative positions of forward arm 32 and rearward arm 42 to each other, is shown in a position for a right-handed person. The thumb lever 52 is pivotally connected to the rearward arm 42 by a pin 53. A thumb lever for a left handed user will be a mirror image of thumb lever 52 which will then be installed on the opposite side of rearward arm 42 from that shown in FIGS. 1 and 2.

Describing now the control mechanism 50, in addition to the aforementioned thumb lever 52, a trigger 54 and palm grip 55 make up the basic control structure, however, these basic control structure elements cause the control through other connected elements as hereinafter described.

The palm grip 55 is rigidly affixed to the rearward arm 42, which is channel-like, by fitting the horizontal portion of palm grip 55 within said channel-like rearward arm 42 and securing it in place by at least two suitable means 49.

Trigger 54 is pivotally connected to the rearward arm 42 by a pin 51. Trigger 54 may have a smooth finger surface 56, or it may be finger grip formed (not shown). Trigger 54 has a clearance stop 57 to clear pin 53.

Trigger 54 and palm grip 55 may be wood, metal, plastics, fiber, or any other suitable material.

Turning now to the connected elements of the control mechanism 50 that are connected to the thumb lever 52 and the trigger 54 for operating the double acting jaws 20 and the hinged relationship of the forward arm 32 to the rearward arm 42, the thumb lever 52 control system will be described first, following by the trigger 54 control system.

Thumb lever 52 has a vertical portion 60 which acts similar to a bell crank when the thumb lever 52 is depressed. As thumb lever 52 is depressed the vertical portion 60 swings toward the rearmost end 44 in a small arc. As the vertical portion 60 swings in an arc it draws with it the connecting rod 62. The connecting rod 62 is connected to the center of a first pin 61 which is free to move in the journal-like holes 63 in the two side flanges of the vertical portion 60. The connecting rod 62 may be connected to said first pin 61 by threaded or other means. A slot 64 in the face of vertical portion 60 maintains connecting rod 62 in a more or less central position and thereby prevents said first pin 61 from escaping from the journal-like holes 63 in the two side flanges of the vertical portion 60.

The distal end of connecting rod 62 connects to a second pin 65 in a manner similar to the connection to said first pin 61. Second pin 65 has a sleeve 66 over it on the inside of yoke-like indexing detent 68. It is to be noted that the sleeve 66 is one method by which second pin can be kept in place in yoke-like indexing detent 68. Other suitable means are within the scope and intent of this invention.

The yoke-like indexing detent 68 is pivotally mounted on the rearward arm 42 by a pin 67. As the yoke-like indexing detent 68 swings through an arc similar to the aforementioned description for vertical portion 60 when the thumb lever 52 is depressed, because the connecting rod 62 then pulls the yoke-like indexing detent 68 rearward, the indexing finger 69 (on the yoke-like indexing detent 68) is withdrawn from whichever indexing slot 70 it is located at the time. It is to be noted that a plurality of indexing slots 70 are located in the index plate 72. Each index slot 70 provides a specific location and angle for the forward arm 32 in relation to the rearward arm 42. The index plate 72 is connected to the outside of one of the gusset plates 38 on the forward arm 32 by the same connecting means 39 used to connect to gusset plates 38 to the forward arm 32.

A tension spring 74, connected between the horizontal portion of the yoke-like indexing detent 68 and the forwardmost distal end of the rearward arm 42, maintains the indexing finger 69 in the selected index slot 70 until thumb lever 52 is depressed to withdraw it.

In actual use, if the forward arm 32 is in the downward position it may be brought to the upward position merely by swinging the gripping device 10 with the thumb lever 52 depressed, so that the forward arm 32 swings upward and then quickly releasing the thumb lever 52 as it reaches the top of the swing, so that the indexing finger 69 drops into an index slot 70 as it passes and holds the forward arm 32 in that position.

An alternative method is to press the double acting jaws section 20 against the floor or some object with the thumb lever 52 depressed so that the forward arm 32 is brought into line with the rearward arm 42. The thumb lever 52 is then released so that the indexing finger 69 can drop into the nearest index slot 50.

When an item is retrieved at a distance, as hereinafter described for the trigger 54 operation, the item or object can be brought to within reach of the user by depressing the thumb lever 52 so that the forward arm 32 drops down to a position at and close to the user. At this point the object can be taken from the jaws section 20 with the free hand, or the object can be dropped into the lap of the user if only one hand is operative or available.

Turning now to the trigger 54 operation to control the operation of the double acting jaws 20, refer to FIGS. 1, 2, and 3.

When the trigger 54 is pulled back toward the palm grip 55, the double acting jaws 20 will close, as hereinafter described. The spring 35, which tends to spring outward, holds the double acting jaws 20 in an open position until the trigger 54 is pulled in order to close the double acting jaws 20. The spring 35 pushes the inboard ends 21 of the jaws 22 and 24 in an outward direction and thus, maintains the double acting jaws 20 in an open position.

When the trigger 54 is pulled and moved toward the palm grip 55, as noted by the arrows at 76, the cable 78 is pulled across the pulley idler roller 80. The cable 78 is anchored to the trigger 54 by a suitable means 82. The pulley idler roller 80 turns freely on a pin-type shaft 84. The cable 78 passes over other similar rollers 86 and 88. A typical roller is shown in FIG. 4.

The end of the cable 78 looped around the spring 35 where the spring 35 passes through the forward arm 32 at the slot 34. The cable 78 is then doubled back upon itself and suitably clipped to itself by a clamp-like clip 90.

Because slack or stretching may occur in the cable 78, a small "C" type take-up wire is provided within the channel side of the forward arm and about which the slack portion is wrapped to make the cable taut. The "C" take-up wire 92 is shown in FIG. 5, but is not shown in FIG. 3.

It is to be noted that the cable may be cord, nylon, linen, steel, or any other suitable material. Any such variation is within the scope and intent of this invention.

Thus, as the trigger 54 is pulled, the cable 78 is drawn back across the pulley idler rollers 80, 86, and 88, which in turn pulls on spring 35, which then pulls the inboard ends 21 of the jaw flat pieces 22 and 24 to the rear and the scissors-like action closes the jaws 22 and 24 to clamp around or on the object to be picked up or lifted.

The gripping device 10 can be used to pick up a can 95 from a shelf 97. It can also pick up a coin or other small objects from a floor.

It is to be noted that the cross section of the forward arm 32 and the rear arm 42 are shown as channel shaped, other cross section configurations may be used and such variations are within the scope and intent of this invention.

Likewise the cross section of the jaws 22 and 24 may be varied as a lamination of flat pieces, a solid piece, a tubular cross section, or other similar shape.

A magnet may be included as part of a built in structure at the ends of the jaws 22 and 24 for retrieving small ferrous metal parts.

Accordingly, modifications and variations to which the invention is susceptible may be practiced without departing the scope and intent of the appended claims.

What is claimed is:

1. A gripping device to aid handicapped persons in reaching and picking up objects, comprising:
   a gripping means;
   a forward arm member connected to said gripping means;
   a rearward arm member pivotally connected to said forward arm member to bring a gripped object at the distal end of said forward arm member to the position of the user of said gripping device; and
   a control mechanism for controlling said gripping means and the movement of said forward arm member toward the user, said control mechanism including a remote thumb control means for operating said pivotally connected forward arm member and said rearward arm member, said pivotal connection causing said gripping means to approach the user to deposit said object.

2. The gripping device as recited in claim 1, wherein said gripping means is a pair of jaws operating scissor-like to lift and retrieve an object.

3. The gripping device as recited in claim 1, and additionally a trigger mechanism in said control mechanism for operating said gripping means.

4. The gripping device as recited in claim 1, wherein said control mechanism includes a plurality of positions of said forward arm member in relation to said rearward arm member, each said position being set forth on an indexed holding means.

5. The gripping device as recited in claim 1, wherein said gripping means are maintained in an open position until said control mechanism closes said gripping means upon the object to be moved.

6. The gripping device as recited in claim 1 and additionally, a means for connecting said rearward arm member to the arm of the user to provide stability of said gripping device during use.

7. The gripping device as recited in claim 1 and additionally, a magnetic insert for said gripping means to facilitate retrieving ferrous objects.

8. The gripping device as recited in claim 1 and additionally, a means connected to said control mechanism for reducing the amount of slack in the operating cable means of the control mechanism.

9. The gripping device recited in claim 1 and additionally, a facing affixed to the interior gripping surface of said gripping means to provide for a secure hold on objects to be lifted.

* * * * *